(12) United States Patent
Robbins et al.

(10) Patent No.: US 8,399,837 B2
(45) Date of Patent: Mar. 19, 2013

(54) APPARATUS FOR MEASUREMENT OF GAS CONCENTRATIONS IN BREATH

(75) Inventors: Peter Allistair Robbins, Oxford (GB); Graham Hancock, Oxford (GB); Robert Peverall, Oxford (GB); Grant Andrew Dedman Ritchie, Oxford (GB)

(73) Assignee: Isis Innovation Limited, Oxford (GB)

( * ) Notice: Subject to any disclaimer, the term of this patent is extended or adjusted under 35 U.S.C. 154(b) by 0 days.

(21) Appl. No.: 13/129,726

(22) PCT Filed: Nov. 13, 2009

(86) PCT No.: PCT/GB2009/002654
§ 371 (c)(1),
(2), (4) Date: Jun. 10, 2011

(87) PCT Pub. No.: WO2010/058150
PCT Pub. Date: May 27, 2010

(65) Prior Publication Data
US 2011/0302992 A1    Dec. 15, 2011

(30) Foreign Application Priority Data

Nov. 19, 2008    (GB) .................................. 0821188.0

(51) Int. Cl.
*A61B 5/083*    (2006.01)
*G01J 5/02*    (2006.01)
(52) U.S. Cl. ..................... 250/339.13; 250/343; 600/532
(58) Field of Classification Search ............... 250/338.1, 250/339.01, 339.02, 339.03, 339.06, 339.07, 250/339.12, 339.13, 343, 352; 422/84; 600/529, 600/532, 543; 73/23.2, 23.3
See application file for complete search history.

(56) References Cited

U.S. PATENT DOCUMENTS

| 6,131,571 A | 10/2000 | Lampotang et al. |
|---|---|---|
| 6,599,253 B1 | 7/2003 | Baum et al. |
| 6,884,222 B1 | 4/2005 | Braig |
| 2003/0109795 A1 | 6/2003 | Webber |
| 2004/0210154 A1 | 10/2004 | Kline |

FOREIGN PATENT DOCUMENTS

| EP | 0692222 A1 | 1/1996 |
|---|---|---|
| WO | WO-99/61895 A1 | 12/1999 |

(Continued)

OTHER PUBLICATIONS

Mikhail Mazurenka, Andrew J. Orr-Ewing, Robert Peverall and Grant A. D. Ritchie: "Cavity ring-down and cavity enhanced spectroscopy using diode lasers," Annual Reports on the Progress of Chemistry, Section C, vol. 101, 2005, pp. 100-142.

(Continued)

*Primary Examiner* — Mark R Gaworecki
(74) *Attorney, Agent, or Firm* — Harness, Dickey & Pierce, P.L.C.

(57) ABSTRACT

A device for measuring oxygen uptake and carbon dioxide production by a respiring subject based on the use of absorption spectroscopy. An absorption spectrometer using cavity enhanced absorption spectroscopy at 763 nm to measure oxygen concentration and direct absorption or wavelength modulation spectroscopy at 2.0035 μm for carbon dioxide concentration is incorporated into a breathing tube in proximity to the respiring subject. This provides measurements of oxygen and carbon dioxide concentration with a good temporal resolution which can be combined with measurements of flow rate as a function of time to obtain oxygen uptake and carbon dioxide production on a breath-by-breath basis. The device can also measure the concentration of water vapor and of anaesthetic gases in exhaled breath.

27 Claims, 4 Drawing Sheets

FOREIGN PATENT DOCUMENTS

| WO | WO-02/17991 A2 | 3/2002 |
|----|----|----|
| WO | WO-03/015631 A1 | 2/2003 |
| WO | WO-2005067515 A2 | 7/2005 |
| WO | WO-2008074142 A1 | 6/2008 |

OTHER PUBLICATIONS

Baschant, D., Stahl, H: "Temperature resistant IR-gas sensor for CO2 and H2O" Sensors, 2004: Proceedings of IEEE (Oct. 24-27, 2004 Vienna) (University of Technology, Vienna, Austria), pp. 142-145 vol. 1.

International Search Report for PCT/GB2009/002654, mailed Feb. 3, 2010.

Search Report Under Section 17(5) of the International Property Office for GB 0821188.0, mailed Mar. 19, 2009.

L. Menzel et al. "Spectroscopic detection of biological NO with a quantum cascade laser." Applied Physics B Lasers and Optics. pp. 859-863. Apr. 20, 2001.

APPARATUS FOR MEASUREMENT OF GAS CONCENTRATIONS IN BREATH

CROSS-REFERENCE TO RELATED APPLICATIONS

This application is a 371 U.S. National Stage of International Application No. PCT/GB2009/002654, filed Nov. 13, 2009. This application claims priority to British patent application No. 0821188.0 filed with the Intellectual Property Office on Nov. 19, 2008, which is herein incorporated by reference in its entirety.

The present invention relates to the measurement of the concentration of molecular oxygen, or carbon dioxide, or molecular oxygen and carbon dioxide together as a function of time in inhaled and exhaled breath, in particular with a view to measuring the oxygen uptake and carbon dioxide production by a respiring human or animal subject.

The accurate measurement of oxygen consumption in a respiring human or animal subject is useful for assessment of both cardiopulmonary and metabolic function. The measurement of carbon dioxide production is useful in assessing metabolic function. Both measurements are useful in medical or veterinary applications such as during anaesthesia or artificial or assisted ventilation of a subject, and during exercise stress testing which has both medical and sports applications.

Currently there are a variety of ways of measuring oxygen concentration. For example, oxygen sensors based on electrochemical cells, polarography, paramagnetism and zirconium oxide are all known for detecting oxygen, but generally these have to be positioned remotely from a subject because they are unsuitable for inclusion within a ventilation tube or airway, and they also have a relatively slow response time. Similar considerations apply to measuring carbon dioxide concentrations, which is almost invariably undertaken using absorption within the infrared spectrum. Mass spectrometers have also been used to measure both the oxygen and carbon dioxide concentration in breath, but because of their large size and weight, again they need to be positioned remotely from the patient. Mass spectrometers are also relatively expensive and delicate and not particularly suitable for use in the average clinical or sports environment.

Nevertheless, analysers based on these technologies have been used in monitoring oxygen and carbon dioxide in breath, for example during anaesthesia, but the positioning of the analyser remotely from the patient means that it is not possible to produce measurements that can be temporally aligned with sufficient accuracy with flow measurements to calculate oxygen consumption and carbon dioxide production by direct integration of the product of concentration and flow over time. In general the analyser is connected to the breathing tube of the patient by a catheter and a pump is used to transport as through the catheter to the analyser and this introduces variable delay times in the arrival of gas at the analyser. There may also be further problems with the concentration measurement in that there can be longitudinal mixing of the gas in its journey from the breathing tube to the analyser, making the concentration measurement less accurate. Thus, analysers used in this configuration (sampling gas via a catheter, from a patient's breathing tube) can provide the temporal profile of the carbon dioxide and oxygen in the breathing tube, but not in a way that can be used to determine oxygen consumption and carbon dioxide production with any degree of accuracy.

A way of working around this problem to some extent has been to connect the patient's breathing tube as a branch from a high (fixed) flow rate gas supply of a known fixed composition (almost always air). The expired gas from the patient mixes back with the high flow rate gas supply and the two are fed to a chamber where they are mixed up by a fan and the concentration of oxygen is measured. The fan chamber is large enough to stabilise the concentration of oxygen and the average oxygen consumption can be calculated by multiplying the fixed high flow rate of gas by the difference between the original oxygen concentration in the incoming gas and the oxygen concentration value in the mixing chamber. However, the method relies on the use of the fan chamber to smooth out variations and thus the temporal resolution of the system is inherently poor. It is therefore impossible to calculate oxygen consumption and carbon dioxide production on a breath-by-breath basis. The system also will not function if the patient is breathing anything other than a fixed gas composition, so is not suitable for use in anaesthesia where low (variable) gas flow rates may also be required.

It would be useful to be able to measure the oxygen consumption and carbon dioxide production on a breath-by-breath basis under conditions when the total flow may be low and/or variable and also under conditions when the inspiratory gas composition may be varying. In principle this can be achieved by measuring the gas flow rate through the breathing tube and multiplying this instantaneous flow rate by the instantaneous gas concentration and integrating over a breath. However, the fact that the concentration measurements are only made after variable catheter delay means that this calculation cannot give reliable results with current gas analysers.

EP-A1-0692222 discloses a sensor for measuring oxygen concentration in breath by absorption spectroscopy, but it uses a multipath cell in which a light beam traverses a zig-zag path between two mirrors positioned in an airway. The present method differs from a multipass arrangement, and has the advantage of simpler alignment and higher sensitivity.

U.S. Pat. No. 6,884,222 discloses apparatus for measuring respiratory quotient which is the ratio of the increase in carbon dioxide concentration to the reduction in oxygen concentration in exhaled breath, but neither oxygen consumption nor carbon dioxide production can be calculated from a knowledge of this ratio alone.

It would therefore be useful to have a way of measuring oxygen consumption, and preferably carbon dioxide production too, accurately on a breath-by-breath basis.

Accordingly the present invention provides apparatus for measuring respiratory oxygen consumption in the breath of a human or animal subject, comprising:
- a breathing tube for provision in an airway for the subject,
- an absorption spectrometer for measuring the concentration of molecular oxygen in gas passing through the breathing tube;
- a flow meter for measuring the rate of flow of gas through the breathing tube; and
- a processor for receiving the concentration and flow rate measurements and adapted to calculate from them and to output breath-by-breath measurements of oxygen consumption;

wherein the absorption spectrometer comprises:
- an optical cavity disposed in the breathing tube in proximity to the subject and through which said gas passes, a light source for supplying light to the optical cavity and a light detector for detecting light emerging from the optical cavity, thereby to provide a signal representative of the absorption of the light by molecular oxygen in the gas in the optical cavity, and wherein the optical cavity and light source are arranged such that the light in the optical cavity retraces some or all of its path to excite one or more resonant modes in the optical cavity to provide cavity enhancement of the oxygen absorption signal.

The term "cavity enhancement" is used in this document to refer to techniques whereby the signal available due to spectroscopic absorption by a target substance present in an optical cavity is enhanced through repeated reflection of the radiation back along the same path within the cavity so as to excite one or more resonant modes. This allows trace components in the gas phase to be much more easily detected and their presence quantified. An optical cavity is usually provided by two optically opposed high reflectivity mirrors (reflectivity typically greater than 99%), and the repeated retracing of some or all of the optical path leads to resonant and interference effects and observable energy density build up. Thus optical cavities are fundamentally different in nature and construction to optical multipass cells which are not resonant and in which careful alignment of mirrors permits a light beam to follow an extended, but well-defined single path between the entry and exit windows of the cell.

The use of an optical cavity within a cavity enhanced absorption assembly enables a high sensitivity to be achieved within a far more compact and lightweight breath analysis apparatus than could be achieved using an equivalent optical multipass cell. The resulting apparatus is also easier to set up and align.

A number of different cavity enhanced absorption techniques are known in the art. Some of these are discussed in the review "Cavity ring-down and cavity enhanced spectroscopy using diode lasers" by Mazurenka et al. *Annual Reports on the Progress of Chemistry—Section C* 101, pp. 100-142 (2005). In cw-cavity ringdown techniques an optical resonance is established in an optical cavity before the light from the optical source is extinguished or the resonance condition removed. The decay time of the cavity resonance, which depends on both the properties of the cavity and the absorptive properties of gas phase components within it, is then measured.

Alternatively, a continuous wave source may be used and the level of resonance continuously measured. In preferred embodiments of the present invention a tunable laser or more particularly a tunable continuous wave laser diode source is scanned in frequency, using a frequency controller or sweep generator. By scanning the optical source sufficiently quickly to limit the overlap between the source frequency and each natural cavity mode to a timescale shorter than the ringdown time of the cavity, resonant peaks in the output signal due to build-up of energy in natural cavity modes are largely avoided. The optical source wavelength and position of one of the cavity mirrors may also be simultaneously modulated to randomise the occurrence of cavity modes which are then lost when averaging the signal over a number of frequency scans of the source. Instead of scanning, discrete frequencies could in principle be used, selected to include absorption lines of target substances.

Thus in an embodiment of the present invention, the wavelength of the light supplied to the optical cavity is scanned to excite multiple resonant modes without allowing energy to build-up in any single mode. In this embodiment the light source continuously supplies light to the optical cavity and the light detector and processor combine the output over a plurality of scans of the wavelength to provide a relatively flat frequency response with high sensitivity to absorption at any spectral line within that wavelength scan. One of the cavity mirrors can also be dithered (vibrated) to ensure excitation of many different modes and thus flatten the frequency response.

Alternatively the cavity ringdown technique can be used in which a single mode of the cavity is excited by the incoming light, which is then turned off, and the decay time of light in the cavity is measured.

Preferably the absorption spectrometer is adapted to measure the concentration of carbon dioxide in the gaseous sample passing through the breathing tube; and the processor receives the carbon dioxide concentration measurements and calculates from them and the flow rate measurements a breath-by-breath measurement of carbon dioxide production. Thus both oxygen consumption and carbon dioxide production measurements can be provided.

The present invention allows an absorption spectrometer to be positioned directly in the breathing tube close to the subject so that the problems of longitudinal mixing of gases and also transit delays as found with prior art systems using catheters and pumps, are eliminated. Further, the use of an optical cavity excited with multiple modes allows the relatively weak oxygen absorption signal to be detected with high speed, sensitivity and accuracy. This is achieved because in an optical cavity, in stark contrast to a multipass cell such as a Herriott cell, the mirrors are arranged so that the light retraces the same path repeatedly between the mirrors, causing some degree of interference and increasing signal sensitivity.

The light source and light detector and also the processor can be remote from the patient with optical fibres being used to couple the optical cavity to the light source or detector. This means that the components that need to be attached to the breathing tube are relatively light, so that the patient feels little additional discomfort from the use of the monitor apparatus. In contrast to multipass systems, e.g. using the Herriot configuration, the mirrors are smaller and lighter, and the incoming and exiting light passes through them. In addition the cavity components and assembly can be made from non-metallic parts for use within MRI instruments.

The carbon dioxide measurement can be made by direct absorption spectroscopy or by wavelength modulation spectroscopy. The oxygen and carbon dioxide measurements can be made using two separate light sources, or by the same light source if a light source which is capable of emitting at suitable different wavelengths is used. Similarly one common light detector or two different light detectors can be used.

The optical cavity is preferably defined by two mirrors positioned so that the optical axis of the cavity is transverse to the breathing tube (though other orientations relative to the breathing tube are possible) and a light is guided to and from the optical cavity by use of optical fibres. The mirrors may be transparent to the wavelength used for carbon dioxide measurement, in which case the mirrors can be used as windows for the light for the carbon dioxide measurement. Alternatively, separate windows can be provided for the carbon dioxide measurement spaced from the optical cavity. Where the mirrors are used as windows for the carbon dioxide measurement the same optical fibres can be used to guide the light for both the oxygen and carbon dioxide measurements.

The oxygen concentration measurement is preferably made using the line at about 763 nm and the carbon dioxide measurement using the line at about 2 μm e.g. at 2.0035 μm.

To achieve the excitation in the optical cavity of multiple modes the wavelength of light being used for the oxygen concentration measurement is rapidly scanned typically over 0.05 nm, for example at a frequency of approximately 1 kHz with measurements being made over an averaging time of typically less than 100 milliseconds and preferably over about 10 milliseconds, or about several tens of milliseconds (for example about 50 to 60 milliseconds). Thus this effectively integrates the signal over several tens of scans thus increasing the sensitivity.

The flow meter may be a conventional flow meter, or an ultrasonic device, positioned in the breathing tube, and by multiplying the instantaneous flow rate and concentration values together, and integrating over time, breath-by-breath measurements of oxygen consumption and carbon dioxide production can be made.

The mirrors may be heated to avoid condensation. Further, a heater may be provided in the path of gas flowing through the breathing tube to the optical cavity, and preferably also in the path of gas flowing out of the optical cavity, to heat the gas to maintain a stable temperature, for example of about 40 C, in the optical cavity and avoid noise. The heater or heaters may comprise multiple passageways through which the gas flows, the passageways being defined within a metallic component in contact with a heat source. This may be achieved by having the gas pass through an array of closely packed metal capillary tubes, or the passageways may be created by rolling one or several pieces of corrugated (or creased) metal foil so as to resemble a Swiss-roll through which the gas passes axially between the layers of the roll. The roll or assembly of capillaries may be mounted within a metal housing with heating elements attached to the housing.

Another embodiment of the invention further includes a light source and detector adapted to measure the concentration of an anaesthetic gas in breath. For an anaesthetic such as isoflurane the absorption is broad and so a broadband light source, e.g. a LED or SLED (superluminescent) is used, or several (two or more) lasers can be used to gain selectivity. Monitoring is conducted in the mid IR region, e.g. around 3.3 microns, or more preferably near IR region. For nitrous oxide $N_2O$, which has sharper absorption features, a cavity enhanced or modulation spectroscopy technique can be used to probe transitions between 1.94 and 2 microns, or a single pass technique as used for the carbon dioxide measurement can be used for transitions between 2.8 and 2.9 microns.

The invention extends to methods of measuring the concentration of oxygen and carbon dioxide, and/or anaesthetic gases in breath by using an optical cavity arrangement as described above.

The invention will be further described by way of example with reference to the accompanying drawings in which.

Figure 1:
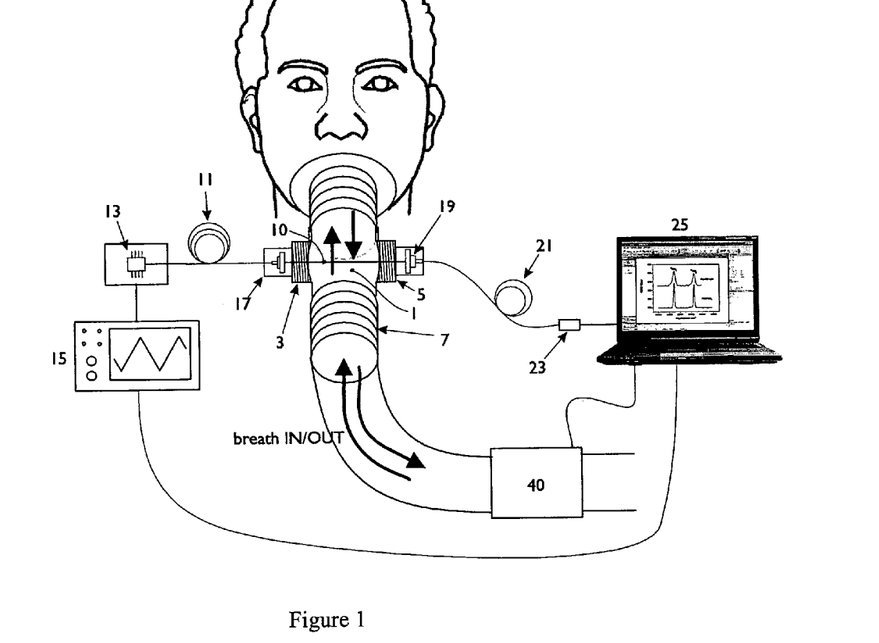
FIG. 1 is a schematic diagram showing an embodiment of the invention.

FIG. 1 schematically illustrates an oxygen and carbon dioxide monitor in accordance with one embodiment of the invention. As can be seen from FIG. 1 the invention allows the measurements to be made directly, only a few centimeters away from the subject, and the measurements are made a non-invasive fashion in that the device can be incorporated into a normal breathing tube such as a ventilation or anaesthetic tube. These advantages mean that the measurements are made in real time every few tens of milliseconds and that there is no time lag between the concentration and flow measurements. Appropriate biological filters placed between the subject and the device will allow multiple use without sterilisation.

The invention utilizes cavity enhanced absorption spectroscopy (CEAS) near 760 nm for the oxygen measurement and direct absorption or wavelength modulation spectroscopy near 2 μm for the carbon dioxide measurement. These give a sensitivity sufficient to determine oxygen partial pressures to within 5 Torr and carbon dioxide partial pressures to within 1 Torr, giving a precision of about 1% measurement of the oxygen uptake in a time of ~20 ms.

As illustrated in FIG. 1 the apparatus utilises an optical cavity 1 formed by positioning two mirrors 3 and 5 on either side of the breathing tube 7 separated by a distance of approximately 4 cm. The mirrors are preferably plano-concave, of diameter of approximately 2 cm and with radii of curvature considerably greater than their separation. The mirrors are arranged so that normals to their mid points are approximately coincident on a common axis called the optical axis 10. It should be noted that one of the mirrors need not be plano-concave as long the cavity remains optically stable.

The mirrors are coated such that the concave surfaces are highly reflective to light of the wavelength used for measuring oxygen concentration (in this embodiment approximately 760 nm) for example 99.99% reflective and the plano surfaces are uncoated or anti-reflection coated.

As illustrated in FIG. 1 the mirrors are mounted relative to the breathing tube such that the optical axis is perpendicular to the gas flow in the breathing tube. However other orientations are possible.

Preferably the mirrors are heated to approximately 10° C. above ambient temperature either by electrical heaters connected to their mirror mount or by a flow of warm gas over their back surfaces. This prevents water from breath being deposited on the surfaces and interfering with the measurements. The mirrors are held in position by adjustable mirror mounts which allow them to be aligned accurately.

As illustrated in FIG. 1 light for both the oxygen and carbon dioxide measurements is delivered to the optical cavity by fibre optic cable 11 from a diode laser light source 13. The diode laser 13, such as a DFB (Distributed FeedBack) laser, or a VCSEL (vertical cavity surface emitting laser), is controlled by a controller 15. The light is introduced to the optical cavity through a coupler 17 such that it enters the cavity through the mirror 3. The light is approximately aligned along the optical axis and this entrance alignment together with the alignment of the mirrors is arranged so that multiple transverse modes are excited within the optical cavity 1. As discussed below the wavelength of the light is also rapidly scanned so that multiple modes are sequentially excited.

Light injected into the optical cavity 1 by the coupler 17 undergoes many reflections within the cavity. The optical source 13 is scanned repetitively over the same spectral range to build up a low noise spectrum within the optical cavity. Light is coupled into the optical cavity whenever a resonance occurs between a source frequency and a cavity mode. The mode structure of the optical cavity can be made as congested as possible by mis-aligning the mirrors of the cavity slightly so that many higher order modes can be excited. Coincidences between the frequency of the optical source 13 and the cavity modes can be further randomised by oscillating the cavity length or by superimposing a jitter on the frequency scan of the source.

Preferably, over a single frequency scan of the optical source 13, several tens of free spectral ranges of the optical cavity are covered, and many cavity modes are sequentially excited. The time constant of the optical detector 23 can be arranged such that adjacent cavity modes are no longer discretely observed, so that in a single frequency scan a relatively smooth signal is obtained. Hundreds of sequential scans can be averaged together to increase the signal to noise ratio and to let any randomisation processes smooth mode structures which would otherwise be apparent in the data.

Absorption by oxygen within the optical cavity 1 is detected by a decrease in the signal output by the optical detector 23. At a particular frequency, the average intensity of the signal is proportional to the ringdown time of the optical cavity, and thus is inversely proportional to optical losses of the cavity. It is important, when using this technique, that significant radiation fields do not build up inside the cavity. If they do, then rapidly fluctuating output spikes may occur at the optical detector output as cavity modes come into resonance with the optical source, which are detrimental to the smooth output signal otherwise achieved by rapid frequency scanning of the optical source 13.

Light is allowed to exit the optical cavity 1 through the second mirror 5 by virtue of its 0.001% transmissivity and this exiting light is coupled by coupler 19 into an optical fibre 21 for delivery to a photodetector 23. The light detector 23 (and 23a below) can be a silicon or a InGaAs photodiode.

The frequency of the light from the diode laser 13 is continuously and rapidly scanned by means of the controller 15 so that many transverse and longitudinal modes of the cavity are excited during each scan and so that no individual mode builds up an appreciable intensity. Thus in the absence of any particular absorber in the cavity the light intensity in the cavity (and thus detected by photodetector 23) would have a relatively flat frequency response. However, when an analyte such as oxygen which has an absorption feature within the wavelength range being scanned is present within the cavity, the light intensity at that particular absorption frequency will fall, thus producing a CEAS spectrum for display on the output controller and display 25. The light source controller 15 and output controller and display 25 can be integrated into a single control system.

As illustrated in FIG. 1 the diode laser 13 and detector 23 are both housed remotely from the breathing tube, and connected to it only by the optical fibres 11 and 21. This reduces the number of components that have to be attached to the breathing tube, which improves comfort for the patient. However, it is clearly possible for the light source and/or photodetector also to be attached to the breathing tube with electrical connections to the control and processing devices.

The wavelength of the laser is preferably scanned using a triangular or saw-tooth waveform at a frequency of approximately 1 Hz and additional modulation may be applied if necessary for signal processing, for example by wavelength modulation spectroscopy. If necessary the light source can be protected from back reflections by use of an optical isolator.

The signal from the photodetector 23 can be electronically filtered if necessary to remove high frequency noise (for example noise at frequencies above 10 kHz).

In this embodiment the diode laser 13 is tuned to a specific rotational transition within the (0,0) band of the $b^1\Sigma_g^+ \leftarrow X^3\Sigma_g^-$ transition in oxygen. The transition is chosen such that all other absorbing features (for example from high overtones or combination bands of $H_2O$, $CO_2$ or other gases present in the ventilation mixture) are absent. The transition is extremely weak, and hence the use of the very sensitive CEAS technique is required for measurements in a ventilation tube.

Scanning the laser electronically some 10-100 times over the transition (over a range of approximately 0.06 nm) produces a signal S of the form:

$$S = \frac{I - I_0}{I} = \frac{\alpha c L}{1 - R}$$

where I and $I_o$ are the intensities of the CEAS signals with and without absorption, respectively, $\alpha$ the wavelength dependent absorption cross section, c the concentration of the species, L is the separation of the mirrors and R the geometric mean of the reflection coefficients of the two mirrors. From measurements of S the concentration c can thus be found if R is known. A sample of air with known oxygen concentration can be used to calibrate the system and determine R.

Figure 2:
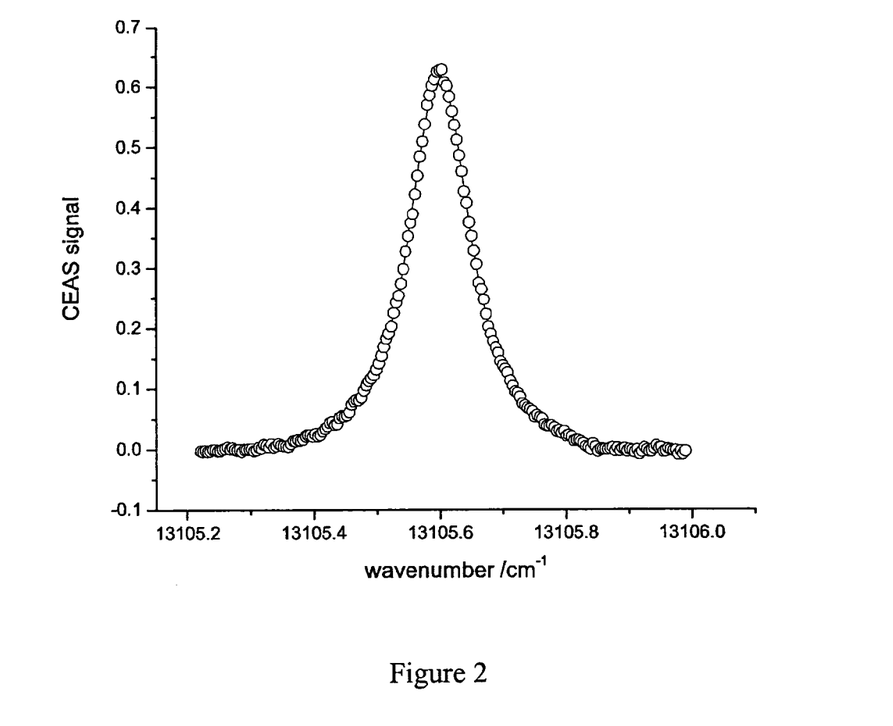
FIG. 2 shows the cavity enhanced absorption signal of oxygen in air as measured by an embodiment of the invention.

FIG. 2 shows an example of the data taken with a flow of atmospheric pressure air with L=4 cm, R~0.999 (99.9%), on the $^PP(5)$ line of the (0,0) band of the $b^1\Sigma_g^+ \leftarrow X^3\Sigma_g^-$ transition. Data were taken over a 6 ms averaging time. Required data for the analysis of the line shape are the integrated absorption cross sections for the transition, and the line broadening coefficients. The former are well known: the latter are tabulated for standard gases, and can be measured (for example using the CEAS technique) for special (e.g.) anaesthetic mixtures. The data of FIG. 2 show a precision off ±1 Torr, well within the 5 Torr precision required.

The carbon dioxide concentration is, in this embodiment, measured by either direct absorption or wavelength modulation spectroscopy at 2.0035 µm on the R18e line of the $v_1+2v_2+v_3$ combination band. Other lines in the 2 µm region may also be used, with the proviso that they are well separated from the absorption features of other gases present, particularly $H_2O$. Light from a VCSEL (vertical cavity surface emitting laser) is directed in a single pass perpendicular to the gas flow, with the laser light being delivered to the breathing tube either through separate windows or through the cavity mirrors 1 and 3. Thus in the FIG. 1 embodiment the same or a different light source 13 can be used to deliver light at a wavelength of 2.0035 µm through the same optical fibre 11 and coupler 17 to the mirror 3 as long as the mirror reflectivity is negligible at this wavelength. Similarly mirror 5 is arranged to be negligibly reflective at this wavelength so that the light can be passed via coupler 19 in an optical fibre 21 to the same, or a different, photodetector 23. Thus in this embodiment single optical fibres are used for delivery of light to and from the breathing tube with the 763 mm and 2.003 µm light being wavelength multiplexed into the same optical fibre.

Figure 1A:
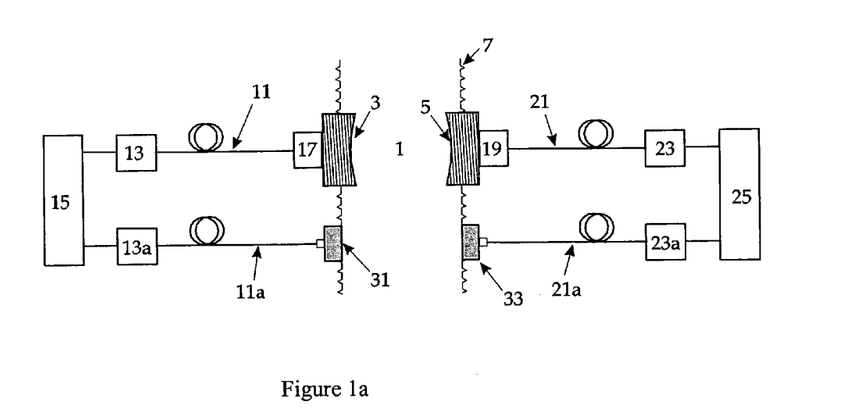
FIG. 1a is a schematic diagram showing an alternative embodiment of the invention.

FIG. 1a illustrates an alternative embodiment in which a separate light source 13a, optical fibre 11a and window 31 are used to deliver the light for carbon dioxide measurement to the breathing tube 7, and window 33 and optical fibre 21a are provided to deliver the light to the separate light detector 23a.

The time resolved direct absorption signals for carbon dioxide are converted into absolute concentrations via the Beer Lambert expression:

$$\frac{I}{I_0} = \exp(-\alpha c L)$$

where the symbols are as before. No calibration is needed.

Figure 3:
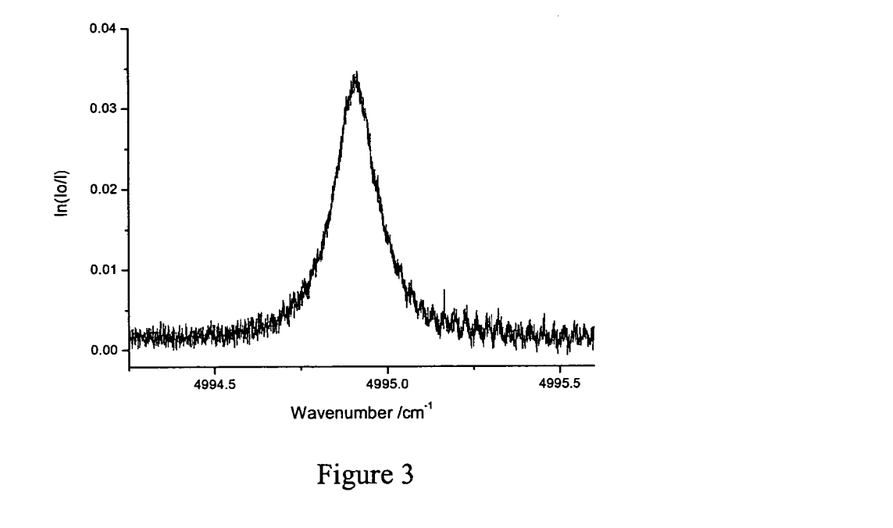
FIG. 3 shows the direct absorption of 7% carbon dioxide in nitrogen taken at 2.003 μm.

Variation of the laser wavelength will produce an absorption spectrum, and an example is given in FIG. 3 of a 7% mixture of $CO_2$ in $N_2$ taken over 10 ms. The values of a are wavelength dependent, and from the absorption and the known values the concentrations c can be found. Required data for the analysis of the line shape are the integrated absorption cross sections for the transition, and the line broadening coefficients. The former are well known: the latter are tabulated for standard gases, and can be measured for special e.g. anaesthetic mixtures.

Figure 4:
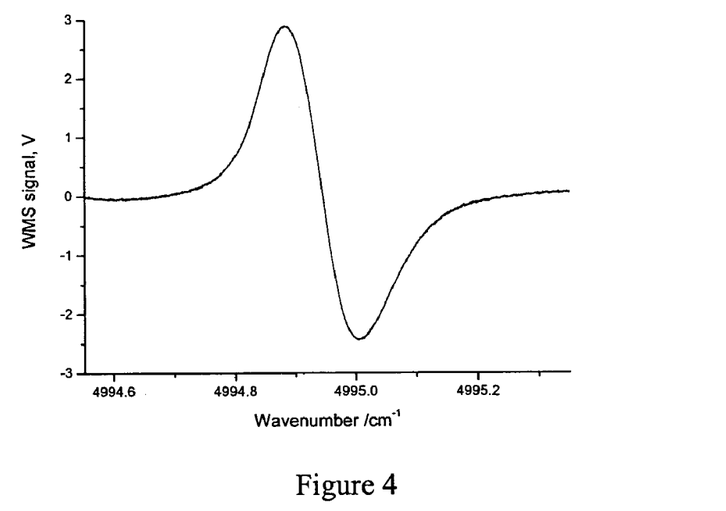
FIG. 4 shows the wavelength modulation spectroscopy signal of $CO_2$ on the same spectroscopic line as FIG. 3.

If increased sensitivity is required, the absorption is measured by wavelength modulation spectroscopy, and FIG. 4 gives an example of the increased signal to noise ratio. Here the signal is either calibrated by use of a sample of known concentration of carbon dioxide, or by using an alternative approach such as a phasor decomposition technique and the recovery of the residual amplitude modulation.

The gas flow is measured using a flow meter 40 such as the NDD Easy One Pro though other conventional flow meters can be used.

Figure 5:
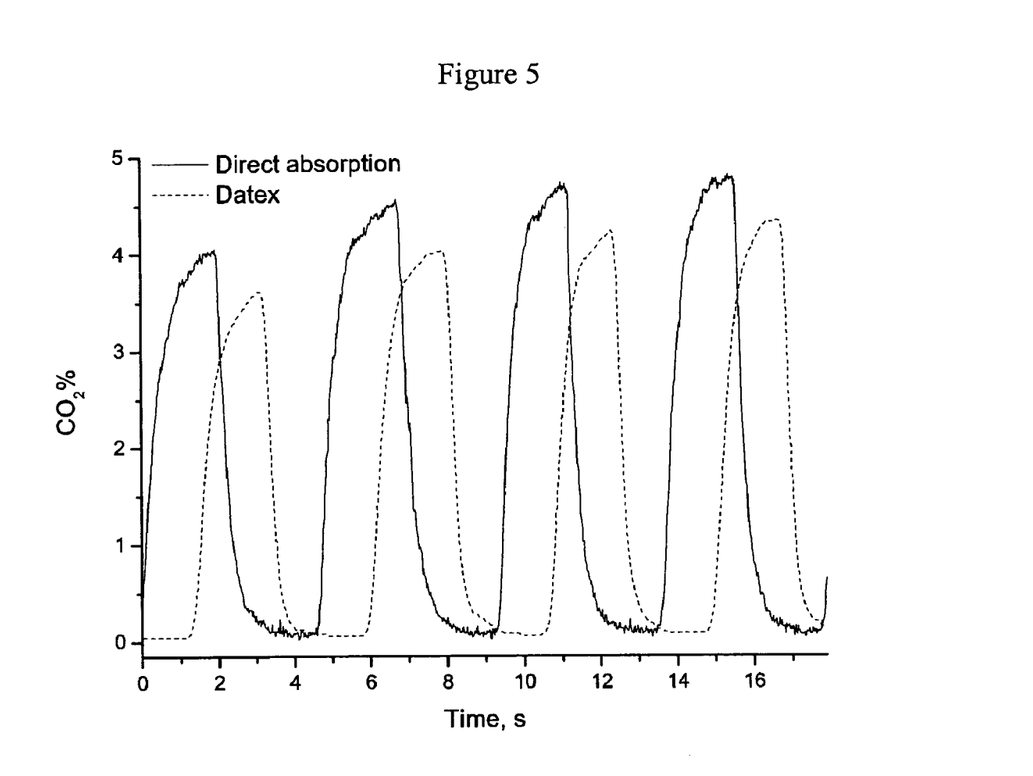
FIG. 5 illustrates the carbon dioxide concentration measurements as a function of time for a respiring subject.

FIG. 5 shows measurements of $CO_2$ concentration during respiration on a time axis, aligned with those from a conventional (i.e. catheter based) $CO_2$ detector. Four breath cycles are shown. The solid line is the experimental data (10 ms resolution) collected using direct absorption in a 4 cm long cell and the dashed line shows the data collected from the conventional (Datex) breath analyser (an instrument used in breath analysis in current medical environments). The plot clearly shows the delay induced in the Datex data due to the use of tubing for sample transport. This shows the importance of truly simultaneous concentration and flow measurements in order to determine absolute values of $CO_2$ production or $O_2$ usage.

Figure 6:
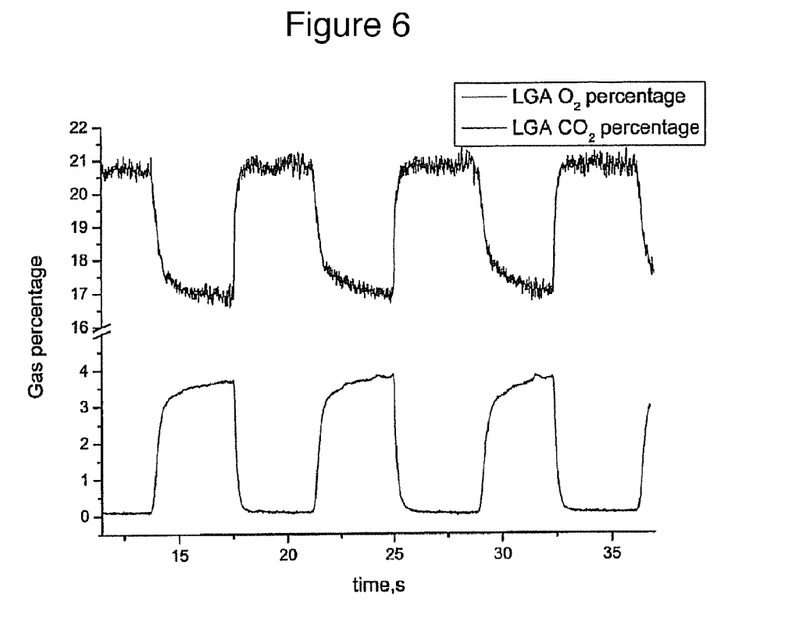
FIG. 6 illustrates simultaneous carbon dioxide and oxygen concentration measurements in exhaled breath as a function of time for a respiring subject.

FIG. 6 shows simultaneous measurements of $CO_2$ and $O_2$ concentration in exhaled breath using an embodiment of the apparatus above. Several breath cycles are shown over a total period of about 35 seconds with a time resolution of 10 ms. The transitions that were probed (spectral lines) were at 760.445 nm and 2.0035 micrometers for the $O_2$ and $CO_2$ respectively.

Figure 7A:
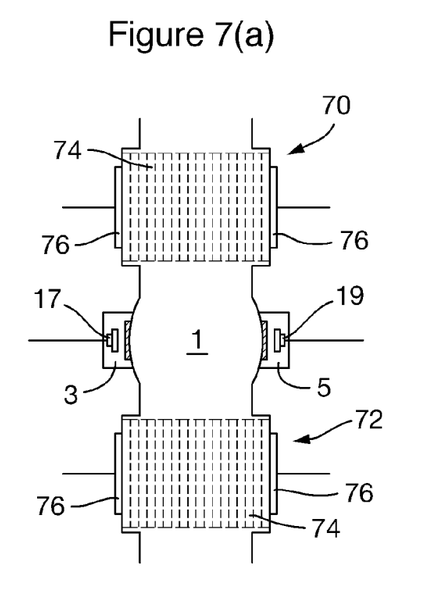
FIGS. 7(a), (b) and (c) illustrate schematically an embodiment including of heaters in the flowpath of gas into and out of the optical cavity.
Figure 7B:
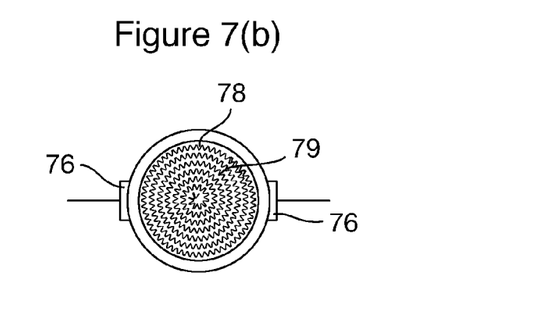
Figure 7C:
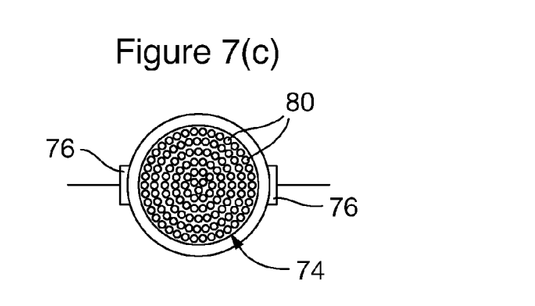

In another embodiment the concentration of water vapour in the breath may also be detected using a single pass absorption measurement (as for the $CO_2$ measurement above) between 1.35 and 1.4 microns, e.g. using the line at 1.368 or 1.392 microns. This may be achieved using another diode laser as a light source to direct light through the cavity mirrors. The detection of the concentration of water vapour, which can be 1 to 6% of the exhaled breath, is advantageous in allowing quantification of $O_2$ and $CO_2$ under different standard water vapour concentrations. FIG. 7 (a) illustrates schematically an alternative embodiment in which heaters 70 and 72 are positioned in the flow path of breath on each side of the optical cavity 1. Maintaining the gas in the cavity 1 at a constant temperature is particularly useful to avoid thermal gradients within the cell which lead to unwanted noise. This is achieved by heating the cavity 1 using a heating element, and also by introducing nested capillary-like baffles 74 in the breathing tube either side of the cavity 1. The baffles 74 are approximately 5 cm long and in one example as illustrated in cross-section in FIG. 7(c) consist of a nested set of fine bore (~1 mm diameter) capillaries 80 (therefore for the size of the breathing tube there are between 300 and 1000 such capillaries all stacked together within the breathing tube). In an alternative as illustrated in cross-section in FIG. 7(b) the baffles 74 can also be made from a foil or foils 78, 79 which can be folded and coiled into a capillary-like arrangement. It is also possible to use thin-walled aluminium tubing.

The baffles 74 are heated by heating elements 76 attached to the outside of a metal housing containing the baffles 74. With the baffles 74 the surface area in contact with the gas is dramatically increased leading to efficient heat transfer. To aid in heat transfer the cell and baffles are made of metal with a good thermal conductivity—aluminium works particularly well as it is easy to machine and has good heat transfer properties.

It is desirable to raise the temperature of the cavity 1 and its components above ~37° C. to avoid condensation on optical components. The baffles 74 enable the desired heating to be achieved while still maintaining a reasonably small arrangement. The length of the baffles on each side of the cavity 1 depends on the initial temperature of the flowing gas, the maximum velocity of the gas and the chosen constant temperature of the cavity 1. For example, for the following conditions: breath flow path of 2.5 cm diameter filled with capillaries with 1 mm diameter, cavity temperature of 40° C., room temperature of 15° C. and maximum flow velocity of 100 liters per minute, the baffle length required to heat the incoming gas is ~8 cm. In the case where the gas flow is coming from the mouth (initial gas temperature is higher, ~35° C.) the baffle length is reduced to ~3 cm. It is also possible to use the pressure change over the length of the baffle 74 measured by a pressure sensor before and after the baffle 74 as a way of measuring the gas flow rates.

The apparatus may also be used to measure the concentration of anaesthetic gases such as isoflurane and nitrous oxide using single pass or cavity-enhanced spectroscopy. Nitrous oxide may be monitored using a laser light source and spectral lines between 1.94 and 2 microns or 2.8 and 2.9 microns, and isoflurane using an LED or SLED light source in the mid or near IR regions.

The invention claimed is:

1. Apparatus for measuring respiratory oxygen consumption in the breath of a human or animal subject, comprising:
   a breathing tube for provision in an airway for the subject,
   an absorption spectrometer for measuring the concentration of molecular oxygen in gas passing through the breathing tube;
   a flow meter for measuring the rate of flow of gas through the breathing tube; and
   a processor for receiving the concentration and flow rate measurements and adapted to calculate from them and to output breath-by-breath measurements of oxygen consumption;
   wherein the absorption spectrometer comprises:
   an optical cavity disposed in the breathing tube in proximity to the subject and through which said gas passes, a light source for supplying light to the optical cavity and a light detector for detecting light emerging from the optical cavity, thereby to provide a signal representative of the absorption of the light by molecular oxygen in the gas in the optical cavity, and wherein the optical cavity and light source are arranged such that the light in the optical cavity retraces some or all of its path to excite one or more resonant modes in the optical cavity to provide cavity enhancement of the oxygen absorption signal.

2. Apparatus according to claim 1 wherein the wavelength of the light supplied to the optical cavity is scanned to excite multiple resonant modes.

3. Apparatus according to claim 2 wherein the light source continuously supplies light to the optical cavity and the light detector and processor combine the output over a plurality of scans of the wavelength.

4. Apparatus according to claim 1 wherein the absorption spectrometer is adapted to measure the concentration of carbon dioxide in gas passing through the breathing tube; and the processor receives the carbon dioxide concentration measurements and calculates from them and the flow rate measurements a breath-by-breath measurement of carbon dioxide production.

5. Apparatus according to claim 4 wherein the absorption spectrometer measures the concentration of carbon dioxide by direct absorption or wavelength modulation spectroscopy.

6. Apparatus according to claim 4 wherein the absorption spectrometer comprises different light sources for measuring the oxygen and carbon dioxide concentrations using light of different wavelengths.

7. Apparatus according to claim 4 wherein the absorption spectrometer comprises a single light source for measuring the oxygen and carbon dioxide concentrations using light of different wavelengths.

8. Apparatus according to claim 7 wherein the single light source delivers light of the two different wavelengths to the optical cavity using a single optical fibre.

9. Apparatus according to claim 4 wherein the same detector is used to detect the light used for measuring both oxygen and carbon dioxide concentrations.

10. Apparatus according to claim 4, wherein the light source emits light at about 2.0035 micrometers to detect the carbon dioxide concentration.

11. Apparatus according to claim 4, wherein separate windows are provided in the breathing tube to pass light for the carbon dioxide concentration measurement.

12. Apparatus according to claim 11 wherein the windows are provided outside the optical cavity.

13. Apparatus according to claim 1 wherein the light source emits light at about 763 nanometers to detect the oxygen concentration.

14. Apparatus according to claim 13 wherein the light source scans the wavelength at about 1 kHz over a wavelength of about 0.05 nm.

15. Apparatus according to claim 1 wherein the optical cavity is formed by 2 mirrors arranged to face each other along a common optical axis which is transverse to the gas flow through the breathing tube.

16. Apparatus according to claim 15 wherein the mirrors are less than 10 cm apart.

17. Apparatus according to claim 15 wherein the mirrors are 3-5 cm apart.

18. Apparatus according to claim 15 wherein the mirrors are about 99.9% to 99.99% reflective to light at the wavelength used to detect the oxygen concentration.

19. Apparatus according to claim 18, wherein at least a portion of the mirrors is transparent at a wavelength used to detect carbon dioxide whereby light of that wavelength can pass through the two mirrors in traversing the optical cavity.

20. Apparatus according to claim 1 wherein the processor is adapted to output a concentration measurement with a time interval no greater than 100 msec.

21. Apparatus according to claim 1 wherein the processor is adapted to output a concentration measurement with a time interval no greater than 50 to 60 msec.

22. Apparatus according to claim 1 wherein the processor is adapted to multiply the flow rate measured as a function of time by the concentration of oxygen measured as a function of time and to integrate over time to find consumption of oxygen on breath-by-breath basis.

23. Apparatus according to claim 1 wherein a heater is provided in the path of gas flowing through the breathing tube to the optical cavity to heat the gas to maintain a stable temperature in the optical cavity.

24. Apparatus according to claim 23 wherein a further heater is provided in the path of gas flowing out of the optical cavity, thereby to maintain a stable temperature in the optical cavity.

25. Apparatus according to claim 23 wherein the heater comprise multiple passageways through which the gas flows, the passageways being defined within a metallic component in contact with a heat source.

26. Apparatus according to claim 1 further comprising a light source and detector adapted to measure the concentration of an anaesthetic gas in the breath.

27. Apparatus according to claim 1 further comprising a light source and detector adapted to measure the concentration of an water vapour in the breath.

* * * * *